United States Patent [19]

Benkwitt et al.

[11] 4,234,568

[45] Nov. 18, 1980

[54] METHOD AND COMPOSITION FOR INHIBITING PLAQUE

[75] Inventors: Frances C. Benkwitt, Yonkers; Fawzy G. Sherif, Stony Point, both of N.Y.

[73] Assignee: Stauffer Chemical Company, Westport, Conn.

[21] Appl. No.: 25,440

[22] Filed: Mar. 30, 1979

[51] Int. Cl.³ .............................................. A61K 7/22
[52] U.S. Cl. ........................................ 424/54; 424/57
[58] Field of Search ................................ 424/48–58, 424/54, 57

[56] References Cited

U.S. PATENT DOCUMENTS

| | | | |
|---|---|---|---|
| 2,955,984 | 10/1960 | Buonocore et al. | 424/57 |
| 3,639,571 | 2/1972 | Turesky et al. | 424/54 |
| 3,666,855 | 5/1972 | Muhler | 424/52 |
| 3,699,220 | 10/1972 | Westrate et al. | 424/52 |
| 3,894,147 | 7/1975 | Bahouth | 424/57 |
| 4,022,887 | 5/1977 | Harris et al. | 424/128 |
| 4,088,752 | 5/1978 | Muhlemann et al. | 424/57 |
| 4,132,773 | 1/1979 | Best et al. | 424/57 |
| 4,144,320 | 3/1979 | Hernestam et al. | 424/54 X |
| 4,146,607 | 3/1979 | Ritchey | 424/54 |
| 4,146,608 | 3/1979 | Ritchey | 424/54 |

OTHER PUBLICATIONS

C.A. 78 #66823n, (1973).
C.A. 73 #80508s, (1970), 78 #128414r, (1973), 85 #186515e, (1976), 88 #65877c, #131126k, (1978), C.A. 89 #17171s, (1978).

*Primary Examiner*—Shep K. Rose
*Attorney, Agent, or Firm*—Vivienne T. White

[57] ABSTRACT

Plaque formation can be inhibited by contacting teeth with the compounds formed by reacting a long chain aliphatic alkylene amine and trimetaphosphoric acid. The antiplaque inhibitors can be incorporated in a variety of oral preparations, including dental creams, mouthwashes, and the like.

6 Claims, No Drawings

METHOD AND COMPOSITION FOR INHIBITING PLAQUE

BACKGROUND OF THE INVENTION

1. Field of the Invention

The present invention is directed to a method for inhibiting the formation of plaque growth on teeth and to compositions useful in such a method.

2. Description of the Prior Art

Dental plaque is thought to be a contributor to the formation of dental caries. Various types of additives have been proposed in dental preparations in order to inhibit its formation. For example, in U.S. Pat. No. 3,639,571 to S. Turesky such organic phosphorus compounds as N-lauryl ethoxy phosphoramidate, N-lauryl chloromethyl phosphonamidate and their chloromethyl analogs have been suggested as plaque inhibitors. U.S. Pat. No. 3,488,419 to H. W. McCune et al. proposes the use of certain polyphosphonic acids as plaque inhibitors, whereas U.S. Pat. No. 2,955,984 to M. G. Bunonocore et al. suggests the use of alkali metal alkyl phosphates as plaque inhibitors. The use of certain tris(phosphonoalkyl) amines as plaque inhibitors has been suggested by R. F. Medcalf, Jr. in U.S. Pat. No. 3,639,569. More recently, in U.S. Pat. No. 3,894,147 to T. G. Bahouth, the reaction product of a higher fatty alcohol having from 8 to 14 carbon atoms with phosphorus pentoxide has been suggested for such use.

In addition to the foregoing, sodium trimetaphosphate has been taught as being an effective anticaries additive when added to diet J. Dent. Res. 1970, 49(1), 140-44 (Eng.). Metaphosphoric acid ($HPO_3$) has also been tested as an anticaries additive, J. Am. Dental Assoc. 60, 193-97 (1960) and J. Dental Res. 44(3) 549-53 (1965).

SUMMARY OF THE PRESENT INVENTION

The present invention is a method of inhibiting the formation of dental plaque by contacting the teeth with an effective amount of the compounds formed by reacting a long chain aliphatic alkylene primary amine, having from about 16-18 carbon atoms, and trimetaphosphoric acid ($H_3P_3O_9$). The structure of the compounds formed as a result is:

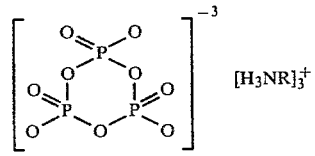

where R is a long chain alkylene group having from about 16-18 carbon atoms.

The mole ratio of amine to acid should be from about 2.9-3.1 moles of amine to from about 0.9-1.1 moles of acid. Also included within the scope of the present invention are dental preparations (dentifrice compositions) containing an effective amount of this plaque inhibitor.

DETAILED DESCRIPTION OF PREFERRED EMBODIMENTS OF THE INVENTION

The active ingredient of the present invention is the compounds formed by reacting a long chain alkylene amine and trimetaphosphoric acid ($H_3P_3O_9$). The preferred long chain aliphatic amine being a alkenyl group which include the $C_{16}$-$C_{18}$ groups such as an oleyl amine. The amines that are used as reactants with the cyclic trimetaphosphoric acid are preferably the primary amines. The structural formula for these compounds is:

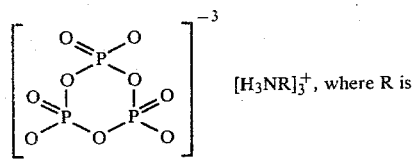

a long chain alkenyl group, desirably a $C_{18}$ alkenyl groups such as oleyl.

The compounds which are useful in practicing the present invention are formed by reacting the selected amine and the trimetaphosphoric acid with one another, e.g., in an organic solvent such as ethanol. The preferred molar ratio of amine to acid should preferably be from about 3 to about 1, and the reaction may be carried out at ambient temperature. These compounds advantageously form amine salts which do not have the unpleasant odor or flavor generally associated with amines.

Broadly, the present invention includes a method of controlling oral conditions, particularly inhibiting plaque formation comprising contacting the teeth with an orally acceptable composition of matter (hereinafter referred to as oral or dental preparations, dentifrice compositions, or just, compositions), containing a herein defined effective amount of a compound of the present invention in intimate mixture with a carrier therefor. The carrier is generally selected from the group consisting of dental creams, toothpowders, liquid dentifrices and mouth washes. The above recitation of known carriers should not be considered to in anyway limit the scope of the invention to those mentioned, as other carriers not mentioned may be suitable for use.

The most convenient carriers to which the compounds of the present invention can be added are mouth washes and dentifrices.

Any suitable substantially water-insoluble polishing agent may be employed in the preparation of dentifrice compositions such as toothpastes, powders, creams, and the like, in accordance with the present invention. There is a relatively large number of such materials known in the art. Representative materials include, for example, dicalcium phosphate, tricalcium phosphate, insoluble sodium metaphosphate, aluminum hydroxide, magnesium carbonate, calcium carbonate, calcium pyrophosphate, calcium sulfate, bentonite, etc., including suitable mixtures thereof. Colloidal dehydrated silica or sodium aluminosilicates may also be used, particularly if the dentifrice is a clear gel. It is preferred to use the water insoluble phosphate salts as the polishing agents and, more particularly, insoluble sodium metaphosphate and/or a calcium phosphate such as dicalcium phosphate dihydrate. In general, these polishing agents will comprise a major proportion by weight of the solid ingredients. The polishing agent content is variable, but will generally be up to about 95% by weight of the total dental composition. In the case of a dental cream, such polishing agents will generally be about 20-75% by weight of the composition, whereas in toothpowders and dental tablets the polishing agents will usually be in greater proportion, such as about 70-95%.

In the preparation of toothpowders, it is usually sufficient to admix mechanically, i.e., by milling, the various solid ingredients, in appropriate quantities and particle size.

In dental cream formulations, the liquids and solids should necessarily be proportioned to form a creamy mass of desired consistency which is extrudable from an aerosol container or a collapsible, e.g. aluminum or plastic tube. In general, the liquids in the dental cream will comprise chiefly water, glycerine, aqueous solutions of sorbitol, propylene glycol, polyethylene glycol 400, and the like, including suitable mixtures thereof. It is advantageous usually to use a mixture of both water and a humectant such as glycerine or sorbitol to keep the formulation from hardening. The total liquid content will generally be about 20-75% by weight of the formulation. It is preferred to use also a gelling agent in dental creams such as the natural and synthetic gums and gum-like materials, e.g., Irish moss, gum tragacanth, sodium carboxymethylcellulose, polyvinylpyrrolidone, starch, and the like, usually in an amount up to 10%, and preferably about 0.2 to 5% of the formulation. These gelling agents aid in imparting a desirable consistency to the dental cream.

In other compositions such as mouth rinses and the like, the aqueous vehicle may comprise from about 20 to as much as 99% of the formulations. In mouthwashes, about 5-30% of alcohol, such as ethyl alcohol, is typically present. Organic surface-active agents or materials used in the compositions of the present invention may be anionic, nonionic, cationic, or ampholytic in nature, and it is preferred to employ as the surface active agent a detersive material which imparts to the composition both detersive and foaming properties. Suitable such detergents are water-soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkyl arylsulfonates, such as sodium dodecyl benzene sulfonate, higher alkyl sulfoacetates, higher fatty acid esters of 1,2dihydroxypropane sulfonates, and the substantially saturated higher acyl amides of lower aliphatic amino carboxylic acid compounds, such as those having from about 12 to about 16 carbons in the fatty acid, alkyl, or acyl radicals, and the like. Examples of the last mentioned amides are N-lauroyl sarcosine, and the sodium potassium and ethanolamine salts of N-lauroyl, N-myristoyl, or N-palmitoyl sarcosinates, which should be substantially free from soap or similar higher fatty acid material which tends to substantially reduce the effect of these compounds. The use of these sarcosinate compounds in oral compositions of the present invention is particularly advantageous, since these materials exhibit a prolonged and marked effect in the inhibition of acid in the oral cavity due to carbohydrates, in addition to exerting some reduction in the solubility of tooth enamel in acid solutions. Desirable surface active effect is obtained with a long chain fatty acid monoglyceride sulfonate such as the sodium salt of hydrogenated coconut oil fatty acid monoglyceride sulfonate used alone or in combination with sodium lauryl sulfate.

Other suitable surface active materials include nonionic agents such as condensates of sorbitan monostearate with up to 60 moles of ethylene oxide, condensates of ethylene oxide with propylene oxide, condensates of propylene glycol ("Pluronics"), and cationic surface active germicides and antibacterial compounds such as di-isobutylphenoxyethoxyethyl, dimethyl benzyl ammonium chloride, benzyl dimethyl stearyl ammonium chloride, tertiary amines having one fatty alkyl group of from 12 to 18 carbon atoms and two polyoxyethylene groups attached to the nitrogen (typically containing a total of from about 2 to 50 ethenoxy groups per molecule) and salts thereof with acids.

It is preferred to use from about 0.05 to about 5% by weight of the foregoing surface active materials in the instant oral preparations.

Various other materials may be incorporated into the oral preparations of the present invention. Examples thereof are coloring or whitening agents, preservatives, silicones, chlorophyll compounds, ammoniated materials such as urea, diammonium phosphate, and mixtures thereof, and other constituents. These adjuvants are incorporated in the instant compositions in amounts which do not substantially adversely effect the properties and characteristics desired.

Any suitable flavoring or sweetening materials may be employed in formulating a flavor for the compositions of the present invention. Examples of suitable flavoring constituents include the flavoring oils, e.g., oils of spearmint, wintergreen, sassafras, clove, sage, eucalyptus, marjoram, cinnamon, lemon, and orange as well as methylsalicylate. Suitable sweetening agents include lactose, maltose, sorbitol and saccharin. Suitably, flavor and sweetening agent may together comprise from about 0.01 to 5% or more of the composition of the present invention.

The compounds which have been found to be effective in accordance with the present invention are present in oral compositions in amounts ranging from about 0.05 to about 5.00%, with a preferred range being from about 0.1 to about 1.00%.

A plaque inhibiting dentifrice composition can be formulated from the following ingredients:

|  | Percent by Weight |
|---|---|
| Dicalcium phosphate dihydrate (Victor grade from Stauffer Chemical Company) | 48.0 |
| Sorbo (70% sorbitol solution) | 17.0 |
| Glycerine (95%) | 10.0 |
| Sodium carboxymethylcellulose (medium viscosity) | 1.0 |
| Ethyl Parasept (Purified ethyl-p-hydroxybenzoate) | 0.1 |
| Saccarin | 0.1 |
| Sodium lauryl sulfate | 1.5 |
| Spearmint oil | 1.0 |
| Water | 20.3 |
| 3-oleylamine 1-trimetaphosphate (reaction product of this invention). | 1.0 |

The following examples are given to illustrate in vitro tests using a compound of the present invention. The examples are presented primarily for the purpose of illustration, and any enumeration or details contained therein are not to be interpreted as a limitation on the invention except as indicated in the appended claims.

EXAMPLE 1

This Example illustrates formation of trimetaphosphoric acid and its reaction with oleylamine to form compounds of the present invention.

Trimetaphosphoric acid was prepared by passing a solution containing 40 gm. of sodium trimetaphosphate in 700 gm. of water, through a 2.54 cm. diameter glass column containing 200 gm. of regenerated "AMBERLITE IR-120" ion exchange resin (from Rohm and Haas Company). The flow rate of the solution was 10 cc./min., and the temperature was ambient. The purity of the trimetaphosphoric acid in the effluent was established by titrating small portions with alkali, once using methyl orange as a pH indicator and once using phenolphthalein as a pH indicator.

Distilled oleylamine, 51.8 gm., (ARMEEN OD, from Akzona, Inc., Armak Chemical Division) was dissolved in 200 ml. of ethanol. The solution of trimetaphosphoric acid that had been previously prepared, was added directly to the oleylamine with stirring at a rate of about 10 ml./min. A white, gummy precipitate began to form and when the pH of the solution reached 4, the precipitate was removed by filtration. The filtered precipitate was shaken with three 200 ml. portions of acetone in a blender and was then allowed to dry by exposure to the atmosphere. This acetone treatment changed the precipitate into a white, free flowing powder with no amine odor. The product had a melting point of 215° C. Elemental analysis verified that the product contained three oleylamine moieties and one trimetaphosphate moiety.

TABLE 1

Analytical Results for 3-oleylamine . 1-trimetaphosphate $(C_{18}H_{35}NH_2)_3 \cdot H_3P_3O_9$

| % | Calculated | Found |
|---|---|---|
| Carbon | 62.22 | 61.58 |
| Hydrogen | 9.89 | 10.69 |
| Nitrogen | 4.03 | 4.23 |
| Phosphorus | 8.91 | 8.10 |

The yield of the purified material was calculated and found to be 78%. The white, odorless powdery product was only very slightly soluble in water at room temperature.

EXAMPLE 2

This Example illustrates the test procedure which was used to test the compound that was synthesized in the preceding Example for plaque inhibition.

The following test procedure was used:
1. Extracted teeth were cleaned with a slurry of zirconium silicate (ZIRCATE, from L. D. Caulk Co.) and while suspended on orthodontic wire, were autoclaved for 15 minutes at 15 lbs./in.$^2$ pressure;
2. The teeth were then manually swirled for 5 minutes in a 1% by weight, aqueous suspension of each of the test chemicals (namely, (a) the compound of Example I, and (b) two control samples described below), in 0.5%, by weight, of polyoxyethylene sorbitan monolaurate liquid emulsifier (TWEEN 21, from Atlas Chemical Industries, Inc.), and were air dried for 2 minutes, and were finally rinsed in sterile distilled water for 2 minutes;
3. The treated teeth were placed in test tubes containing 10 ml. trypticase—5% sucrose broth which had been inoculated with 0.3 ml. of a culture of *Streptococcus mutans* No. 6715;
4. The teeth were incubated anaerobically for 24 hours at 37° C. and were then examined for plaque growth.

Two controls were also used in the tests: (1) an untreated tooth (labelled Control No. 1, below) and (2), a tooth treated with a 1%, by weight, solution of the reaction product of polymeric ethyl metaphosphate with laurylamine ("Victamine C" sold by Stauffer Chemical Company, Specialty Chemical Division, Westport, Connecticut) (labelled Control No. 2 below). A process for manufacturing this latter product is described as being effective in retarding plaque in U.S. Pat. No. 3,639,517 to S. Turesky.

TABLE 2

| Compound Tested | Results |
|---|---|
| Control 1 | Profuse plaque growth on tooth |
| Control 2 | No plaque detected |
| Example 1 | No plaque detected |

What is claimed is:

1. An oral composition for inhibiting plaque formation on teeth which contains an effective amount of from about 0.05% to about 5.0% of a compound formed by reacting a long chain aliphatic alkylene primary amine having from about 16–18 carbon atoms and trimetaphosphoric acid having a molar ratio of from about 2.9–3.1 of the amine to about 0.9–1.1 of the acid wherein the effective amount of the compound is based on the weight of the composition.

2. A method of inhibiting plaque formation by contacting the teeth with an effective amount of from about 0.05% to about 5.0% of a compound formed by reacting a long chain aliphatic alkylene amine having from about 16 to 18 carbon atoms and trimetaphosphoric acid having a molar ratio of from about 2.9–3.1 of the amine to about 0.9–1.1 of the acid and a carrier thereof the effective amount of the compound being based on the weight of the compound and carrier.

3. A method as claimed in claim 2 wherein the molar ratio of amine to acid is 3:1.

4. A method as claimed in claim 2 wherein the amine is oleylamine.

5. The composition as claimed in claim 1 wherein the molar ratio of the amine to the acid is 3:1.

6. A composition as claimed in claim 1 wherein the amine is oleylamine.

* * * * *